(12) United States Patent
Sjolander

(10) Patent No.: US 12,133,051 B2
(45) Date of Patent: Oct. 29, 2024

(54) ELECTRONIC HEARING DEVICE AND METHOD

(71) Applicant: GN Hearing A/S, Ballerup (DK)

(72) Inventor: Maria Lisa Sjolander, Hvidovre (DK)

(73) Assignee: GN Hearing A/S, Ballerup (DK)

( * ) Notice: Subject to any disclaimer, the term of this patent is extended or adjusted under 35 U.S.C. 154(b) by 289 days.

(21) Appl. No.: 17/714,068

(22) Filed: Apr. 5, 2022

(65) Prior Publication Data

US 2022/0353625 A1 Nov. 3, 2022

(30) Foreign Application Priority Data

Apr. 28, 2021 (DK) .......................... PA 202170193
Apr. 28, 2021 (EP) ...................................... 21170830

(51) Int. Cl.
*H04R 25/00* (2006.01)

(52) U.S. Cl.
CPC ........... *H04R 25/50* (2013.01); *H04R 25/305* (2013.01); *H04R 25/43* (2013.01); *H04R 25/554* (2013.01)

(58) Field of Classification Search
None
See application file for complete search history.

(56) References Cited

U.S. PATENT DOCUMENTS

| | | | |
|---|---|---|---|
| 9,497,530 B1 | 11/2016 | Campbell et al. | |
| 2004/0234089 A1* | 11/2004 | Rembrand | H04R 25/30 381/317 |
| 2007/0112279 A1* | 5/2007 | Iseberg | A61B 5/126 600/559 |
| 2008/0285780 A1 | 11/2008 | Aarts | |

(Continued)

FOREIGN PATENT DOCUMENTS

| | | |
|---|---|---|
| DE | 19905743 | 9/2000 |
| DE | 10 2014 108663 | 12/2015 |

(Continued)

OTHER PUBLICATIONS

1st examination report dated Oct. 25, 2021 for Danish patent application No. 202170193.

(Continued)

*Primary Examiner* — Harry S Hong

(74) *Attorney, Agent, or Firm* — Vista IP Law Group, LLP

(57) ABSTRACT

A method performed by an electronic hearing device with an earpiece configured to be worn in an ear, includes: engaging a hearing mode wherein a compensated output signal is based on current hearing compensation data. Performing a first fitting procedure including: obtaining first hearing compensation data via audiometric measurements; emitting an otoacoustic stimulation signal and capturing an acoustic signal including otoacoustic emissions. In response to receiving a first input signal, performing a first monitoring procedure including: emitting an otoacoustic stimulation signal and capturing an acoustic signal including otoacoustic emissions, if any. Determining a deviation value based on the second acoustic signal and the third acoustic signal; and determining whether the deviation value satisfies a first criterion. In accordance with a determination that the deviation value satisfies the first criterion, communicating a first notification signal indicative of the deviation from the hearing device.

20 Claims, 5 Drawing Sheets

(56) References Cited

U.S. PATENT DOCUMENTS

2013/0274628 A1    10/2013  Fausti et al.
2017/0150909 A1*   6/2017   Dalhoff ................ A61B 5/6817
2019/0289409 A1    9/2019   Greenberg et al.
2020/0138340 A1    5/2020   Nadon et al.

FOREIGN PATENT DOCUMENTS

EP          2053877         4/2009
WO     WO 2019/216767       11/2019

OTHER PUBLICATIONS

Extended European search report dated Oct. 20, 2021 for EP 21170830.0.

\* cited by examiner

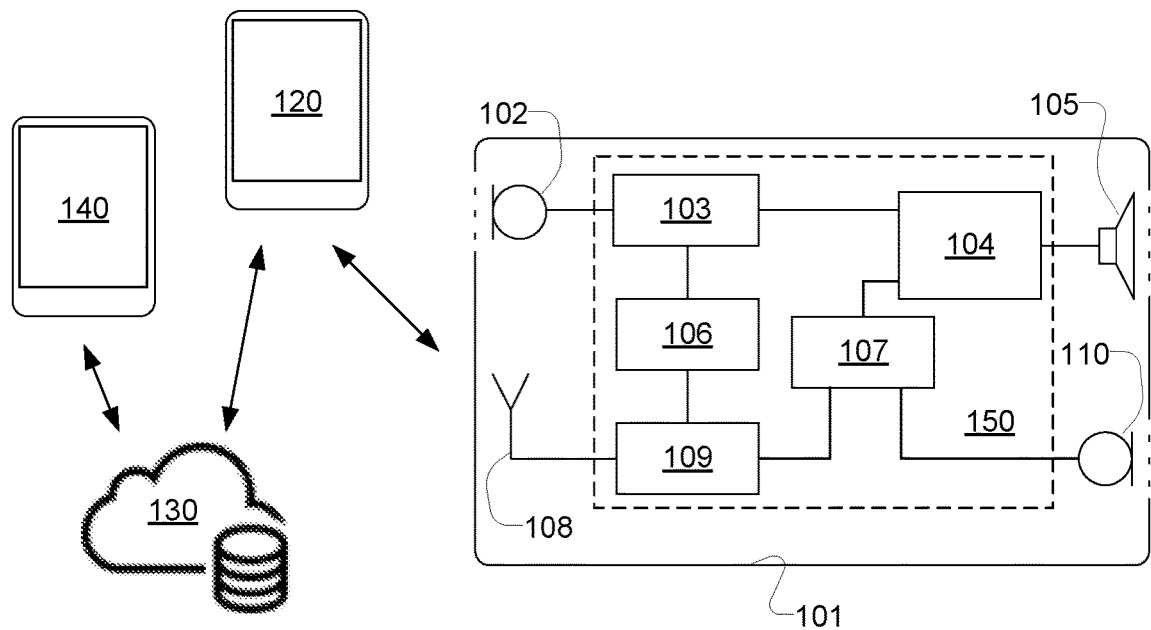
Fig. 1a
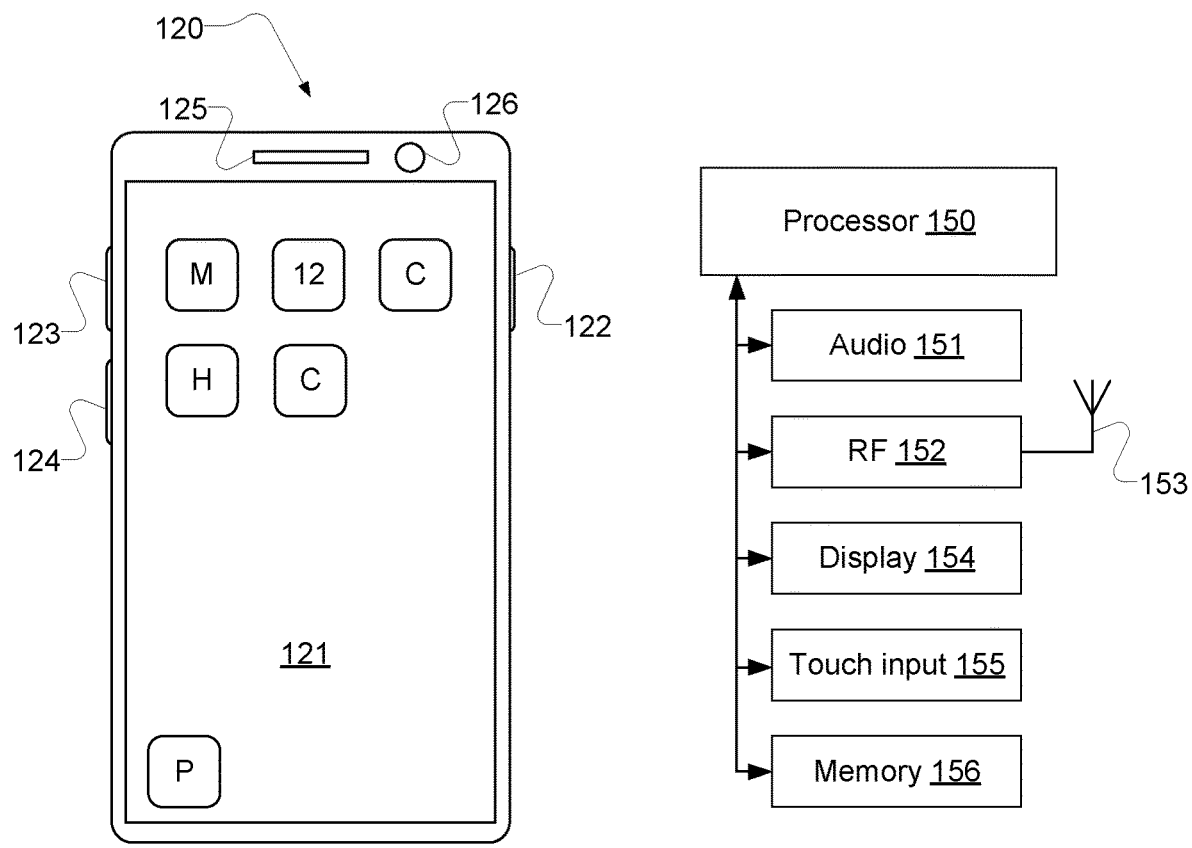
Fig. 1b
Fig. 1c

ELECTRONIC HEARING DEVICE AND METHOD

RELATED APPLICATION DATA

This application claims priority to, and the benefit of, Danish Patent Application No. PA 202170193 filed on Apr. 28, 2021, and European Patent Application No. 21170830.0 filed on Apr. 28, 2021. The entire disclosures of the above applications are expressly incorporated by reference herein.

FIELD

There is provided a method at an electronic hearing device with an earpiece configured to be worn in an ear and including: an acoustic output transducer, a first acoustic input transducer, a second acoustic input transducer; and a processor coupled to the acoustic transducers. The method comprises engaging a hearing compensation mode, including emitting a compensated output signal by means of the acoustic output transducer; wherein the compensated output signal is based on a hearing compensation profile. Further, the method includes performing a fitting procedure including obtaining hearing compensation data via audiometric measurements requiring the wearer's input to confirm a hearing threshold.

BACKGROUND

It is known in the technical field of electronic hearing devices to engage a hearing compensation mode, wherein hearing compensation is performed by the electronic hearing device based on a hearing compensation profile. The hearing compensation profile is obtained by performing a fitting procedure including obtaining hearing compensation data via audiometric measurements requiring the wearer's input to confirm a hearing threshold. Typically, it is required that the user of the electronic hearing device (the wearer) consults a human audiologist who conducts the fitting procedure using specialized equipment to perform the audiometric measurements in cooperation with the wearer. Once the fitting procedure is completed the hearing device is optimized to provide personalized hearing compensation when the hearing mode is engaged.

It has been discovered that so-called otoacoustic emissions (OAEs) can be recorded from the external ear canal using sensitive low-noise microphones. Otoacoustic emissions are low-level sounds that emanate from the cochlea itself e.g. in response to short stimulus impulses.

More specifically, it has been discovered that so-called distortion-product otoacoustic emissions are also generated in the cochlea and emanate therefrom in response to two tones of a given frequency and sound pressure level presented in the ear canal. These otoacoustic emissions are described as distortion products (DP-OAEs) of otoacoustic emissions. DP-OAEs represent mechanical distortion of outer hair cells within a region of overlap of two primary tones with frequencies f1 and f2 and sound pressure levels L1 and L2. These otoacoustic emissions can also be recorded from the external ear canal using sensitive low-noise microphones.

Thus, besides being triggered with short stimulus impulses, otoacoustic emissions can also be evoked at stationary stimulation with two sine tones (primary tones) of the frequency f1 and f2 which are presented at the same time.

Research has shown that otoacoustic emission signals, such as distortion-product otoacoustic emissions, can be measured by a sound probe inserted in the external ear of a user for being input into a computer computing an audiogram providing fitting parameters for a hearing aid compensating for the user's hearing loss in accordance with the audiogram.

U.S. Pat. No. 5,526,819 discloses the recording of distortion product emission (DPE) levels in human beings. At least one microphone and a sound-delivery system is inserted in the external ear canal in a manner similar to that required to position a small hearing aid. Two primary tones Tf1, Tf2 are applied simultaneously to the ear. The cochlea of the inner ear produces a DPE tone which is sensed by the microphone. DPE levels are sensed as a function of input frequencies f1 and f2. Such DPE frequency is equal to 2f1−f2. Such DPE frequencies are collected in 100 Hz steps by adjusting f1 and f2 and maintaining a substantially constant ratio between f1 and f2. Two output forms are created: an DPE audiogram and a DPE input/output function.

U.S. Pat. No. 7,223,245 describes a handheld hearing testing device for automatically assessing loss of hearing sensitivity and compression (recruitment). The handheld hearing testing device employs extrapolated distortion product otoacoustic emission input/output functions (DPOAE I/O-functions) and auditory brain stem responses (ABRs). The hearing testing device has a display screen attached to a handheld device generating and collecting otoacoustic emission signals and/or brain stem response signals into a programmed computer with a clinical audiogram providing fitting parameters for hearing aids calculated on the basis of assessed hearing threshold and compression. For recording DPOAEs, a sound probe has to be inserted in the ear canal. In order to expand the assessment to severe hearing loss, the auditory brain stem responses, ABRs, have to be also recorded. For recording ABRs, electrodes have to be fixed on the scalp. Based upon OAE and ABR measurements, hearing thresholds are constructed and displayed in the audiogram form.

U.S. Pat. No. 9,497,530 discloses an earbud embodiment adapted to be located within the ear canal of one of a user's ears includes two speakers, an internal microphone, and an optional external microphone. Whereas an optional external microphone may be used for noise cancellation, an internal microphone is used for measurement of otoacoustic emissions (OAEs). In particular, two speakers per ear are included to allow measurement of distortion-product otoacoustic emissions. Allegedly, it is possible to increase a user's enjoyment of sound by personalizing an audio signal so that the user perceives the audio signal as if the user had ideal hearing. While the speakers play an audio signal to the user, the sensor records the user's response to the audio signal. The sensor can be a microphone. The user's response can be the audio response inside the user's ear. Based on the measured response, and based on the knowledge of how other people perceive sound, the audio signal is modified to compensate for the difference between the user's hearing and the ideal hearing and/or desired hearing.

However, there is a need for a more convenient way of providing a hearing device with a hearing compensation profile for compensating for a user's hearing loss, let alone a need for a less resource demanding process.

SUMMARY

It has been observed that it is possible to intervene during the course of medical treatment or other procedures or exposures that may affect a person's hearing based on early signs of changes in the person's hearing. However, a change in hearing, typically degraded hearing, is oftentimes not detected in good time to make any meaningful intervention to e.g. preserve or protect a person's hearing. Some reasons may be that other things have a higher priority and that it is inconvenient or practically impossible to monitor sufficiently frequently for a potential hearing loss.

It is an object to provide a method providing screening for changes in otoacoustic emissions to indicate possible reductions in hearing as a result of noise exposure, medical treatment or other ototoxins. In particular, there is provided:

A method performed by a hearing system at least including an electronic hearing device with an earpiece configured to be worn in an ear and including: an acoustic output transducer, a first acoustic input transducer, a second acoustic input transducer, a first wireless communications unit; and a processor coupled to the acoustic transducers; the method comprising;

engaging a hearing mode, including: enabling capturing of a first acoustic signal by means of the first acoustic input transducer, generating a compensated output signal based on the first acoustic signal and emitting the compensated output signal by means of the first acoustic output transducer; wherein the compensated output signal is based on current hearing compensation data;

at a first time, performing a first fitting procedure including:
   obtaining first hearing compensation data via audiometric measurements requiring the wearer's input to confirm a hearing threshold;
   emitting an otoacoustic stimulation signal via the acoustic output transducer and capturing a second acoustic signal including otoacoustic emissions, if any, by means of the second acoustic input transducer;

at least at a second time, in response to receiving a first input signal, performing the first monitoring procedure including:
   emitting an otoacoustic stimulation signal via the acoustic output transducer and capturing a third acoustic signal including otoacoustic emissions, by means of the second acoustic input transducer;
   determining a deviation value based on the second acoustic signal and the third acoustic signal; and determining whether the deviation value satisfies a first criterion;
   in accordance with a determination that the deviation value satisfies (y) the first criterion, communicating a first notification signal indicative of the deviation from the hearing device.

An advantage is that the first notification signal indicative of the deviation from the hearing device is a reliable indicator of a possible hearing loss or a change in hearing. The otoacoustic measurements obtained the second time are reliably comparable to the otoacoustic measurements obtained the first time. Thus, the first notification signal is based on a recurrent and consistently similar type of measurements, namely recurrent otoacoustic measurements. This enables a more robust and reliable determination as to whether an update of the current hearing compensation data is required due to a reliably determined change based on a second criterion. In particular the fitting procedure includes the audiometric measurements and the capture of otoacoustic emissions, if any. Thus, the otoacoustic emissions captured the first time are associated with the generally more reliable audiometric measurements.

An advantage is that the electronic hearing device enables automatically having tests based on the otoacoustic effect performed recurrently by the electronic hearing device, e.g. when at home, e.g. without an Internet connection, e.g. without scheduling an appointment with an audiologist. This may serve as an objective measure of whether degradation of hearing has occurred e.g. during the course of a treatment e.g. in connection with hospitalization. The first notification signal may thus be helpful for the wearer of the hearing device, a caretaker and/or an audiologist.

The audiometric measurements are distinguished from the otoacoustic measurements in that the otoacoustic measurements are based on an autonomous acoustic response originating from the wearer's cochlear. Audiometric measurements require the wearer's conscious, intentional response. Otoacoustic measurements may be carried out without any intervention from the wearer. Audiometric measurements and otoacoustic measurements are based on acoustic stimulation signals e.g. based on one or more tones at varying signal levels.

In some examples, only when significant changes (e.g. large deviation values) are detected, further audiometric measurements performed by a healthcare professional are required, said audiometric measurements requiring the wearer's input to confirm a hearing threshold in order to keep the electronic hearing device updated to the wearer's current hearing ability.

In some aspects, the determining a deviation value is based on comparing the second acoustic signal and the third acoustic signal; and determining whether the deviation value satisfies a first criterion.

In some examples, the hearing mode is engaged before the fitting procedure is performed e.g. based on current hearing compensation data, which have default values e.g. representing a flat (neutral) hearing compensation or representing a mild, typical hearing compensation. In some examples, the hearing mode is engaged only after the fitting procedure is completed. In some examples, the hearing mode is disengaged at times when performing the monitoring procedure. In some examples, the hearing mode is disengaged at times when performing the fitting procedure. The hearing mode may be engaged at a time before the fitting procedure is run a first time, e.g. using a flat hearing compensation profile. The hearing mode may be engaged at a time when the monitoring procedure and/or the fitting procedure is interrupted e.g. interrupted temporarily.

In some examples, the method includes exiting the hearing mode in connection with engaging the first monitoring procedure or suspending the hearing mode during the course of emitting a stimulation signal and capturing the otoacoustic emissions.

A deviation value may be computed at one or more frequencies and/or for one or more frequency bands. In some examples, deviation values are computed for frequency bands or at frequencies corresponding to frequencies at which audiometric measurements are performed. In some examples, the number of frequency bands are in the range of 10 to 50 frequency bands, e.g. 15 or 30 frequency bands.

In some examples a deviation value is computed by aggregating deviations at one or more frequencies or frequency bands. In some examples, a deviation value is based on weighted deviations at one or more frequencies or frequency bands. The first criterion may include a threshold value for each of the one or more frequency bins and/or for the aggregate value. The threshold value may be expressed in dB or in another way.

The first input signal may be a signal received in response to a user input at the electronic hearing device, a timer at the hearing device, or at another device of the hearing system or from a remote server.

In some embodiments, the hearing system further includes an electronic device with a display, first input means, a second wireless communications unit, and a processor.

An advantage is that the electronic device can be programmed to provide at least improved user interface capabilities of the electronic hearing device. In some examples the processor is a programmable processor that can execute or run one or more applications (an app, or multiple apps). In some examples, the electronic device is a mobile or wearable electronic device such as mobile phone, a smart phone, a tablet computer, a smart watch or the like e.g. augmented reality glasses. In some examples, the first input means include a touch-sensitive display and one or more physical buttons. In some examples, the first input means are configured to detect and recognize gestures. The first and second wireless communication units may operate in accordance with a Bluetooth specification and/or a Wi-Fi specification in a manner enabling communication or interoperability. The first wireless communications unit and the second wireless communications unit enable wireless communication between the electronic hearing device and the electronic device. In some examples, the wireless communications units are in accordance with a Bluetooth standard, a Wi-Fi standard or another wireless communications standard.

In some embodiments, the method comprises:
in response to receiving the first input signal, at least the second and/or a further time:
automatically performing the first monitoring procedure without requiring a user's input.

An advantage is that otoacoustic measurements can be carried out, e.g. unobtrusively, without requiring the user's input for initiating the otoacoustic measurements automatically.

In some aspects, the first input signal is a signal from a timer of the hearing device or from another device of the hearing system or from a remote server. In some examples the first input signal is generated at the electronic device. The first input signal triggers performing the first monitoring procedure. In some examples, the method comprises generating the first input signal, to trigger performing the first monitoring procedure at scheduled times or at scheduled intervals. In some aspects, the method comprises generating the first input signal, to trigger performing the first monitoring procedure at scheduled times or at scheduled intervals during a period of time. The method may forgo generating the first input signal at times not falling in the period of time. Thereby, the monitoring procedure can be engaged during times e.g. when the user is subjected to medical treatment and/or exposed to certain ototoxins.

In some embodiments the first fitting procedure comprises:
in accordance with a determination that the second acoustic signal satisfies a second criterion, enabling the first monitoring procedure;
wherein the determining a deviation value and the communicating a first notification signal indicative of the deviation from the hearing device, is performed in accordance with a determination that the monitoring procedure is enabled.

An advantage is that the first monitoring procedure can be enabled only if the wearer has an otoacoustic response. This is the case for almost all people unless they suffer from problems with the inner ear or have excess cerumen in the ear canal. By enabling the first monitoring procedure only if the second criterion is satisfied, it is prevented that possibly misleading first notification signals are communicated.

The second criterion may represent whether the captured otoacoustic emissions are sufficiently strong and/or sufficiently indicative of a person's hearing. The second acoustic signal may be processed for one or more frequency bins. In some examples second acoustic signal is processed by aggregating signal level values across one or more frequency bins. In some examples, signal level values are based on weighted signal level values across one or more frequency bins. The second criterion may include a threshold value for each of the one or more frequency bins and/or for the aggregate value. The threshold value may be expressed in dB or in another way.

In some embodiments the first monitoring procedure includes:
storing data values based on an acoustic signal captured by means of the second acoustic input transducer in response to emitting an otoacoustic stimulation signal via the acoustic output transducer; wherein the data values include or are stored with a date-time value representing the time of capturing the acoustic signal;
wherein the data values are communicated to the electronic device and/or to a server computer.

An advantage is that the data values including the date-time values can be made available to audiologist for analysis of temporal changes in the data values. This may give significant insights into the wearer's hearing loss over time e.g. to determine the current otoacoustic measurement data based on temporal changes such as trends and recurrent variations.

The data values include or are stored with a date-time value e.g. each time the first monitoring procedure is performed. The data values and the date-time values may be stored in a table or database e.g. in a file such as an XML file.

In some embodiments the second fitting procedure includes:
emitting an otoacoustic stimulation signal via the acoustic output transducer and capturing a fourth acoustic signal including otoacoustic emissions, if any, by means of the second acoustic input transducer;
in accordance with a determination that the fourth acoustic signal exceeds a first threshold, enabling the first monitoring procedure.

An advantage is that otoacoustic measurement are performed during the course of performing the fitting procedure and it is thereby possible to relate a hearing loss determined from audiometric measurements to the otoacoustic measurements, which can serve as a basis for determining a deviation therefrom and hence determining that a (further) hearing loss is significant. Thus, a second and/or any further fitting procedure may include otoacoustic tests to keep a basis for assessing a hearing loss at a time between fitting sessions e.g. at a time convenient for the wearer.

In some embodiments the method comprises:
at the electronic device:
at a time following the first time, displaying a first notification prompting the user to engage the first monitoring procedure or displaying a second notification prompting the user to engage a second monitoring procedure.

An advantage is that multiple sets of otoacoustic measurements at different times can be statistically processed to improve the determination whether the deviation is significant.

In some examples, the notification prompting the user to engage the monitoring mode is displayed in a notification centre of an operating system running on the electronic device. Thereby the notification can reach the user despite the user not explicitly opening the first app. In some examples the notification includes the first affordance to engage the monitoring mode directly from the notification.

In some examples, the displaying a notification prompting the user to engage the first monitoring mode is performed recurrently e.g. at regular times or at regular intervals. In some examples, the displaying a notification prompting the user to engage the first monitoring mode is scheduled to take place more frequently during a predefined time period and less frequently at times following the predefined time period. The scheduling enables more frequent testing e.g. during periods of illness and/or scheduled treatment.

In some embodiments, the fitting procedure includes:
in accordance with a determination that the first monitoring procedure is not enabled, and in response to receiving a second input signal at a third time, performing a second monitoring procedure including:
    emitting an otoacoustic stimulation signal via the acoustic output transducer and capturing a second acoustic signal including otoacoustic emissions, if any, by means of the second acoustic input transducer; and
in accordance with a determination that the second acoustic signal exceeds the first threshold, enabling the first monitoring procedure.

An advantage is that the wearer can attempt to have otoacoustic tests performed at the third time despite no otoacoustic response was received during the fitting procedure.

The second input signal is a signal received via a user interface. It is thereby required that the first input signal is a user-initiated request to perform the monitoring procedure.

In some embodiments the method comprises:
at the electronic device:
displaying a second affordance to engage the first monitoring procedure or the second monitoring procedure;
receiving a second input signal via the first input means and communicating the first input signal from the electronic device to the electronic hearing device;
wherein the hearing device is engaged to perform the first monitoring procedure or the second monitoring procedure.

An advantage is that the electronic system is enabled to obtain the otoacoustic measurement data at times when it is deemed relevant and/or convenient by the wearer/user. This greatly improves the comfort and convenience for hearing impaired persons.

In some examples, displaying a first affordance to engage the monitoring mode is performed in response to a user opening a first app. The first app communicates with the electronic hearing device via the wireless communications means.

In some embodiments the method comprises:
storing the current hearing compensation data as a first selectable item in a first repository;
obtaining a current hearing compensation data based on the captured otoacoustic emissions and/or the second hearing compensation data obtained by the fitting procedure performed a fourth time and storing the current hearing compensation data as a second selectable item in a second repository;
enabling the first selectable item and the second selectable item to be selectively engaged as current hearing compensation data.

An advantage is that hearing compensation can be based on accurate hearing compensation data including electing e.g. firstly the second selectable item, then secondly the first selectable item, and then again the second selectable item.

In some examples the wearer initiates, requests or engages then selected item as current hearing compensation data. This is particularly useful in cases when the wearer's hearing loss has a dynamic or changing character.

In some examples the storing, obtaining and enabling are performed before completing the fitting procedure a first time, a fourth time or another time.

In some examples, the first repository is located in memory of the electronic device and/or in memory of the electronic hearing device.

In some embodiments the method comprises:
at the second time or at a third time, in accordance with a determination that the first monitoring procedure is enabled, in accordance with a determination that the deviation values satisfy the first criterion, and in accordance with receiving a fourth input signal:
    updating the current hearing compensation data based on the third acoustic signal and/or second hearing compensation data obtained by a second fitting procedure performed a fourth time.

An advantage is that the wearer can activate an update of the current hearing compensation in situations wherein the first monitoring procedure is enabled and wherein the deviation is significant. In particular when there is a further hearing loss that has degraded hearing following the first fitting procedure and when a fitting procedure is not readily available to the wearer, e.g. considering the wearer's abilities, hearing compensation can anyhow be updated. This may greatly improve quality of life for the wearer.

In some examples, the fourth signal is communicated from the electronic device to the electronic hearing device in response to a user input at an affordance displayed on a user interface of the electronic device. In some examples, the current hearing compensation data are thus updated based on the second hearing compensation data obtained by the second fitting procedure. The method thereby ensures that current hearing compensation data are based on data from a fitting procedure rather than a monitoring procedure. This improves reliability of the current hearing compensation while the current hearing compensation can be updated when there is a further hearing loss that has degraded hearing following the first fitting procedure.

In some examples though the accuracy of hearing loss compensation is determined to be sufficiently high and reliable that the current hearing compensation data can be updated based on the second monitoring procedure or any subsequent monitoring procedure.

In some embodiments the method comprises:
in accordance with a determination that the deviation is significant and in accordance with receiving the fourth input signal, and at least until after updating the current hearing compensation data, one or more times, forgoing performing the fitting procedure the fourth time.

An advantage is that the fitting procedure is at least postponed, while compensation for a hearing loss can be improved until a fitting procedure can be performed. It is possible to both detect a further hearing loss which develops after the first time, when the fitting procedure was performed, and to update the current hearing compensation data, such that hearing compensation is adapted to the further hearing loss until a fitting procedure based on audiometric measurements requiring the wearer's input to confirm a hearing threshold can be performed.

In some aspects, highly accurate first hearing compensation data can be recurrently obtained via audiometric measurements based on automatic or semi-automatic hearing impairment assessments without requiring a physical or online consultation with an audiologist. Whereas the wearer's active participation is required during the course of performing the highly accurate audiometric measurements, only the wearer's passive participation is required during the course of performing the otoacoustic test in the first monitoring mode.

There is also provided a computer-readable storage medium comprising one or more programs for execution by one or more processors of an electronic hearing device with an earpiece, an acoustic output transducer, a first acoustic input transducer, a second acoustic input transducer, a wireless communications unit, one or more processors, and memory; the one or more programs including instructions for performing the method.

A computer-readable storage medium may be, for example, a software package, embedded software. The computer-readable storage medium may be stored locally and/or remotely.

There is also provided an electronic hearing device comprising:
an earpiece;
an acoustic output transducer;
a first acoustic input transducer;
a second acoustic input transducer;
a wireless communications unit;
one or more processors; and
memory storing one or more programs, the one or more programs including instructions which, when executed by the one or more processors, cause the electronic device to perform the method.

BRIEF DESCRIPTION OF THE FIGURES

A more detailed description follows below with reference to the drawing, in which:
FIG. 1a shows a block diagram of an electronic hearing device, a mobile electronic device, and a server computer;
FIG. 1b shows a mobile electronic device with a display;
and
FIG. 1c shows a block diagram of a mobile electronic device.

DETAILED DESCRIPTION

Figure 2:
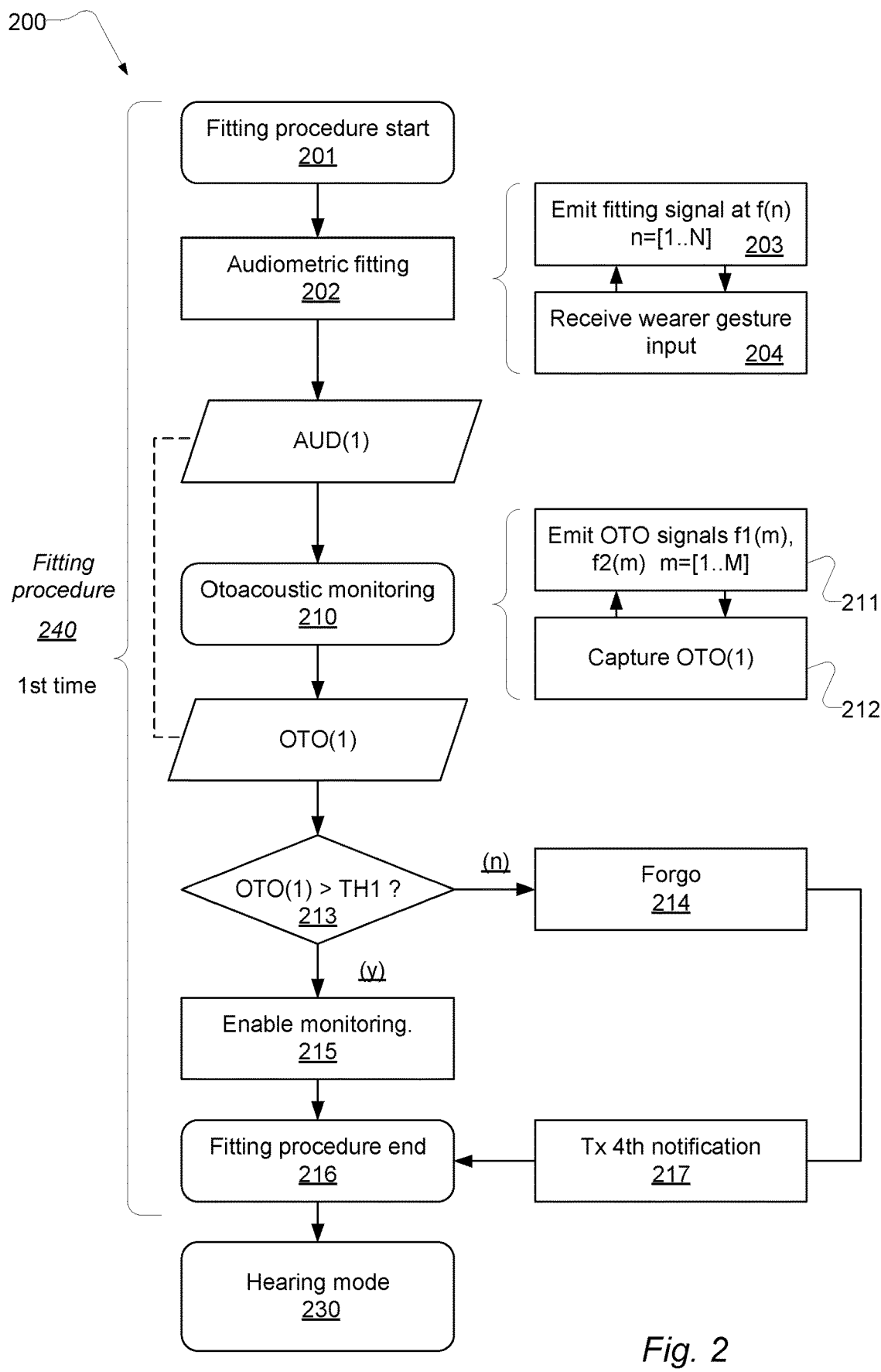
FIG. 2 shows a first flowchart including a fitting procedure and a first monitoring procedure.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1a shows a block diagram of an electronic hearing device 101, a first electronic device 120, a second electronic device 140 and a server computer 130. The electronic hearing device 101 includes wireless communication means such as an antenna 108 and a transceiver 109 for wireless communication with the first electronic device 120 e.g. using a Bluetooth or Wi-Fi protocol or another communications protocol. The first electronic device 120 is configured to communicate with the server computer 130, such as a cloud server, at least occasionally, using a wireless connection e.g. based on a public telecommunications network, such as 3G, 4G or 5G network, and/or a private communications network e.g. based on a Wi-Fi protocol. The first electronic device 120 may be an electronic device, such as a smartphone, possessed by the wearer of the electronic hearing device 101. The first electronic device 120 may be configured with a so-called app (software application) to enhance or add a user interface to the electronic hearing device 101. A second electronic device 140 may be possessed by a human audiologist to perform e.g. fitting procedures and/or supervision of the wearer's hearing e.g. based on recurrently obtained otoacoustic data.

The electronic hearing device 101 comprises an earpiece configured to be worn in the wearer's ear and includes an acoustic output transducer 105, a first acoustic input transducer 102, a second acoustic input transducer 110, a first wireless communications unit 108, such as an antenna; and a processor 150 coupled to the acoustic transducers. The acoustic output transducer 105 may include one or more miniature loudspeaker(s). The acoustic input transducers may each include one or more microphones. The first acoustic input transducer 102 is arranged in the earpiece to capture acoustic waves propagating towards the wearer. The second acoustic input transducer 110 and the acoustic output transducer 105 are arranged in the earpiece to emit and capture acoustic waves in a space established between the earpiece and the wearer's ear canal and the middle ear.

In the hearing mode, the processor 150 captures the first acoustic signal, from the environment surrounding the wearer, by means of the first input transducer 102. A hearing compensation unit 103 of the processor 150 performs hearing compensation using a current hearing compensation profile and outputs a compensated signal to an output unit 104, which outputs the compensated signal to the acoustic output transducer 105 in the hearing mode. Thus, in the hearing mode, a signal path is established from the first acoustic input transducer 102 to the acoustic output transducer 105. The acoustic output transducer is arranged e.g. in the earpiece to emit acoustic signals towards the wearer's eardrum. In some examples the first acoustic input transducer 102 includes a directional microphone, or an array of microphones coupled to one or more beamformers. A hearing profile may be deployed via a hearing mode controller 106.

During an otoacoustic monitoring procedure, the acoustic output transducer 105 emits an otoacoustic stimulation signal and the second acoustic input transducer 110 captures a second acoustic signal including otoacoustic emissions, if any, emitted from the wearer's ear. Thus, the second acoustic signal propagates in the wearer's ear canal. An otoacoustic control unit 107 generates or forwards the otoacoustic stimulation signal via the output unit 104 and processes the otoacoustic signals received via the second acoustic input transducer 110. During the otoacoustic monitoring procedure the hearing mode may be suspended. The acoustic output transducer 105 may include one or more miniature loudspeakers.

During a fitting procedure, the electronic hearing device 101 may be engaged to perform audiometric measurements and generate stimulation signals e.g. in interaction with the first electronic device 120 and/or the second electronic device 140 and/or the cloud server 130.

In some examples, the otoacoustic stimulation signals are generated in the first or second electronic device. In some examples, the otoacoustic stimulation signals are generated in the electronic hearing device.

FIG. 1b shows a first electronic device 120 with a display 121. The first electronic device 120 may have similar elements as the second electronic device 140. The electronic devices 120, 140 are, in some examples, mobile electronic devices as depicted or wearable electronic devices e.g. including a smart watch, a tablet computer or another type of computer. The electronic device 120 includes a touch-sensitive display 121, physical input buttons 122, 123 and 124, a camera lens 126 for a built-in camera (not shown) and a loudspeaker opening 125. The electronic device 120 displays a set of icons and/or affordances designated 'M', '12', 'C', 'H', 'C' and 'P'. An affordance, as known in the art of graphical user interfaces, has a graphical icon and properties that help a user understand that they can interact with it, and the type of interaction that may be involved. For instance, the affordance 'C' may be tapped to activate an application, e.g. an app, that is engaged to perform portions of the method described herein.

FIG. 1c shows hardware elements of the electronic device 120; The hardware elements comprise a processor 150 that may include a combination of one or more hardware elements. In this respect, the processor 150 may be configured to run one or more a software programs or software components thereof including the application that can be activated via the affordance 'C'. The processor 150 is coupled to an audio circuit 151, a radio frequency circuit 152, including one or more antennas 153, a display 154, which may be display 121, a touch input circuit 155 and a memory 156.

FIG. 2 shows a first flowchart 200 for a method including a fitting procedure and a first monitoring procedure. Following completion of the fitting procedure and the first monitoring procedure, the hearing mode is engaged in step 230 based on the result of at least the fitting procedure. In some examples, the hearing mode is engaged a first time, before completion of the fitting procedure and the first monitoring procedure, e.g. based on a default hearing profile such as a flat hearing profile.

The method is performed by an electronic hearing device e.g. as described in connection with FIGS. 1a-1c and including an earpiece configured to be worn in an ear and including: an acoustic output transducer, a first acoustic input transducer, a second acoustic input transducer, a first wireless communications unit; and a processor coupled to the acoustic transducers.

For the sake of completeness, the hearing mode, includes capturing a first acoustic signal by means of the first acoustic input transducer, generating a compensated output signal based on the acoustic signal and emitting the compensated output signal by means of the first acoustic output transducer. The compensated output signal is based on current hearing compensation data.

The first fitting procedure is started in step 201. The first fitting procedure includes both of audiometric fitting performed in step 202 as it is known in the art of hearing aids and otoacoustic monitoring performed in step 210. The first fitting procedure thus includes obtaining first hearing compensation data via audiometric measurements requiring the wearer's input to confirm a hearing threshold. As exemplified by steps 203 and 204 this includes playing a fitting signal f(n) such as a tone at a predefined amplitude and frequency and in response thereto receiving the wearer's gesture input to confirm or not whether the fitting signal was perceived heard by the wearer. The steps 203 and 204 are repeated at various frequencies and at various amplitudes, e.g. several times at each frequency and amplitude such as three times. The frequencies may include 125 Hz, 250 Hz, 500 Hz, 1 KHz, 2 KHz, 4 KHz and 8 KHz or fewer or more frequencies. The amplitudes may be varied in steps of 3 dB or more or less.

Further, the first fitting procedure includes performing otoacoustic monitoring in step 210. Generally, compared to a conventional audiometric procedure, the otoacoustic test is faster and does not require the wearer to respond orally or by gestures. The otoacoustic test can therefore be performed, e.g. automatically. This is useful e.g. when the wearer is a patient under serious medical treatment and is weakened in physically e.g. mentally affected.

As exemplified by steps 211 and 212 this includes emitting an otoacoustic stimulation signal via the acoustic output transducer and capturing a second acoustic signal including otoacoustic emissions, if any, by means of the second acoustic input transducer. The otoacoustic stimulation signal may include one or more tones e.g. two tones at the same time at frequencies $f1(m)$ and $f2(m)$ to stimulate otoacoustic distortion products as it is known. In response thereto, at the same time or immediately after, an otoacoustic response, if any, is measured. The stimulation is repeated at different frequency pairs f1, f2, wherein f2 is e.g. a function of f1, e.g. f2 is 2 times f1. In some examples the amplitudes of the stimulation signals are each fixed or set at a pre-set value. In some examples, e.g. in about 25% of a population, the wearer's ear does not produce an otoacoustic response. This is however mainly due to wax in the ear canal and/or problems with the inner ear.

Following completion of the otoacoustic monitoring in step 210, or following stimulation at one or more frequency pairs or one or more amplitude pairs, the captured signals or data based thereon are stored as data OTO1 in step 212.

Further, in step 213 it is determined whether the captured signals or data based thereon, stored as data OTO1, exceeds a first threshold. This enables testing whether an otoacoustic response was generated, or at least detectable, in the wearer's ear. In the affirmative (y) event thereof, a monitoring procedure is enabled in step 215. It is then possible, at a later time, to verify whether an otoacoustic response was generated and to enable an otoacoustic monitoring procedure at a later time. In the non-affirmative (n) event, the method forgoes enabling the monitoring procedure or disables the monitoring procedure in step 214. A notification, e.g. a fourth notification is displayed in step 217 to indicate the absence of an otoacoustic response. Step 217 may be omitted.

Subsequently, the fitting procedure including the otoacoustic monitoring procedure is completed in step 216 and current hearing compensation data are deployed at the electronic hearing device to enable hearing compensation in accordance with the result of the fitting procedure.

The hearing mode can then be engaged or re-engaged in step 230.

Figure 3:
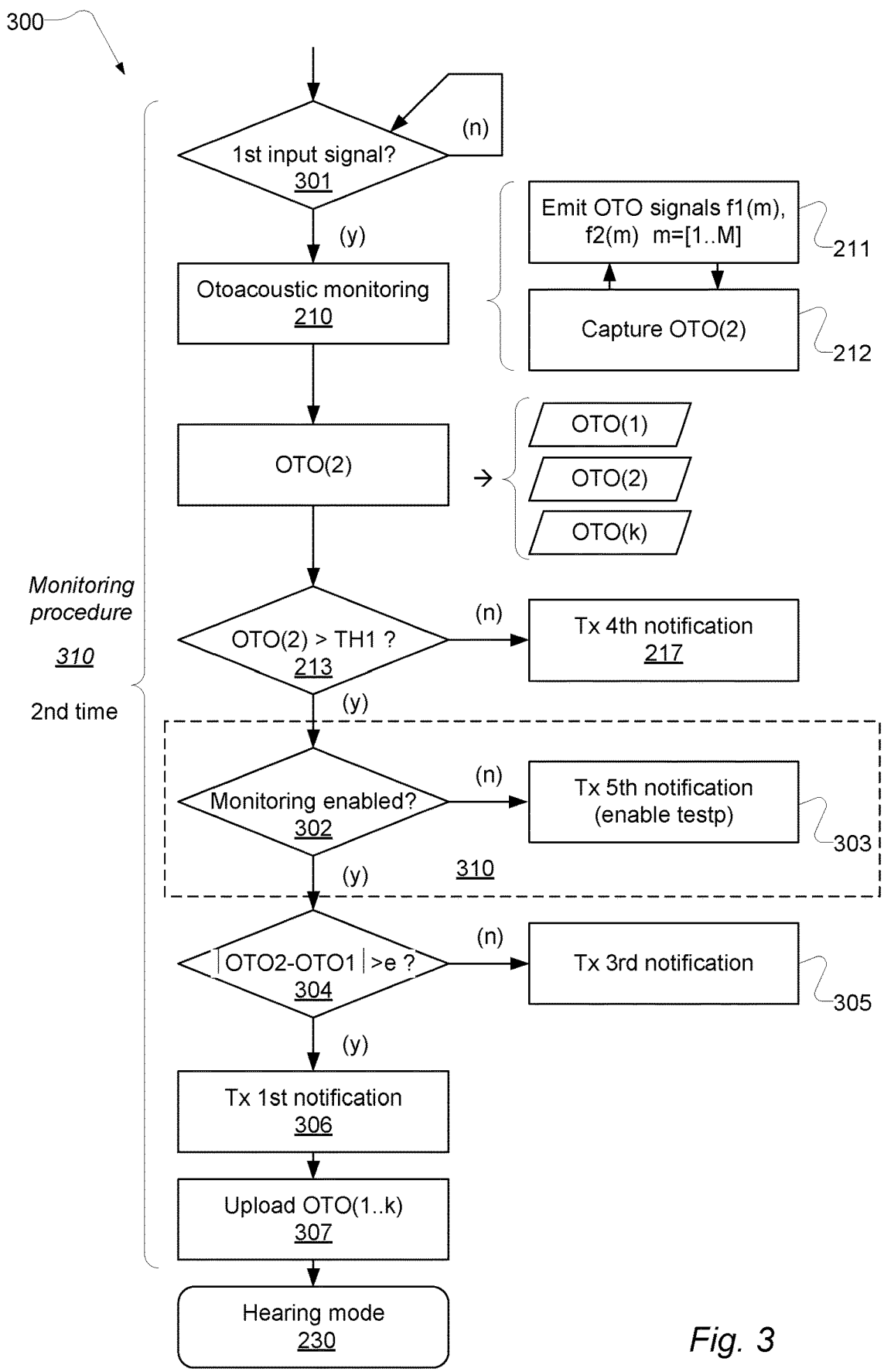
FIG. 3 shows a second flowchart including a second monitoring procedure.

FIG. 3 shows a second flowchart 300 including a second monitoring procedure 310. Whereas the first monitoring procedure is performed in connection with a fitting procedure, the second monitoring procedure is performed in response to receiving a first input signal. In an example the first input signal is a signal received in response to a user's or wearer's input e.g. at an affordance displayed on the first electronic device 120.

The second monitoring procedure includes performing otoacoustic monitoring in step 210 as described above. Also, as exemplified by steps 211 and 212, this includes emitting an otoacoustic stimulation signal via the acoustic output transducer 105 and capturing, this time, a third acoustic signal including otoacoustic emissions, if any, by means of the second acoustic input transducer 110. The captured signals or a data value based thereon are designated OTO(2). Also, in step 213 it is determined whether the captured signals, or a data value based thereon, OTO(2), exceeds the first threshold, TH1. In the non-affirmative event (n) of step 213, a $4^{th}$ notification may be transmitted in step 217, e.g. to the first electronic device 120 or the second electronic device 140. The $4^{th}$ notification may inform the wearer and/or an audiologist that an otoacoustic response is not detectable and/or sufficiently strong.

In the affirmative event (y) of step 213, it is tested in step 302 whether the monitoring procedure was enabled based on a previous test, e.g. in connection with the first fitting procedure. In the non-affirmative event (n) of step 302, in step 303 a $5^{th}$ notification may be generated and/or the monitoring procedure may be enabled for subsequent monitoring procedures. In the affirmative event (y) of step 302 the method tests in step 304 whether the most recent otoacoustic response e.g. OTO(2) deviates, e.g. significantly, from a previous or preceding otoacoustic response e.g. OTO(1). In the non-affirmative event (n) of step 304, i.e. that there is no deviation or no significant deviation, a $3^{rd}$ notification is transmitted, e.g. to the first electronic device, in step 305. In the affirmative event (y) of step 304, a $1^{st}$ notification is transmitted in step 306 e.g. to the first electronic device and/or to the second electronic device e.g. via a server computer. The most recent otoacoustic response e.g. OTO(2) or a set of otoacoustic responses may be transmitted or uploaded to the server computer in step 307. Thus, in accordance with a determination that the deviation value is significant, the method communicates a first notification signal indicative of the deviation from the hearing device. In some examples determining whether the deviation is significant is based on the so-called Kullback-Leibler divergence. determining whether the deviation is significant is based on a sum of differences e.g. a weighted sum of differences.

In some embodiments, the test regarding whether monitoring is enabled is omitted. Then steps 302 and 303 in box 310 are omitted.

In some examples, the captured otoacoustic signals or data based thereon are stored with a date-time value, e.g. a time-stamp, each time a monitoring procedure is performed e.g. as data items OTO(1), OTO(2), OTO(k), . . . . The data items are communicated to the first electronic device and/or the second electronic device e.g. via a server computer. Thereby, the data items including the date-time values can be made available to an audiologist for analysis of temporal changes in the data values. In step 306 the data items OTO(1), OTO(2), OTO(k) may be uploaded individually in response to being obtained or at times when an upload connection becomes available.

When the second monitoring mode is completed or interrupted e.g. following transmission of a notification in steps 217, 303 or 305, the method may proceed to engage the hearing mode in step 230.

Figure 4A:
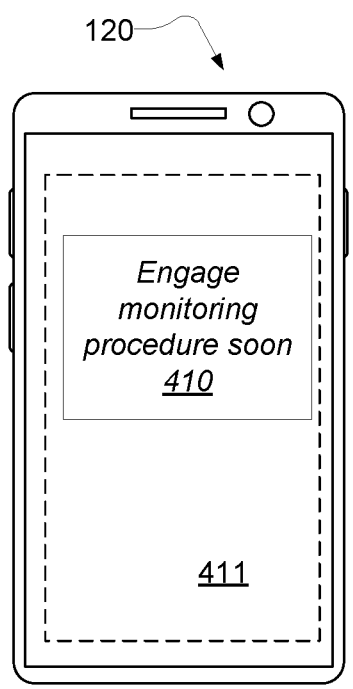
FIGS. 4a and 4b show examples of user interfaces.
Figure 4B:
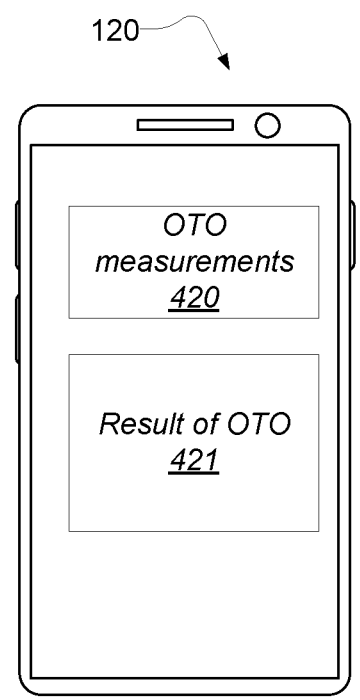

FIGS. 4a and 4b show examples of user interfaces.

In FIG. 4a a notification 410 to engage in a monitoring procedure is displayed in a notification centre 411. The notification centre 411 may be a part of the operating system of the electronic device.

In FIG. 4b a report 421 with results of an otoacoustic monitoring procedure is shown e.g. including a graphical audiogram in response to activation of an affordance 420.

Figure 5:
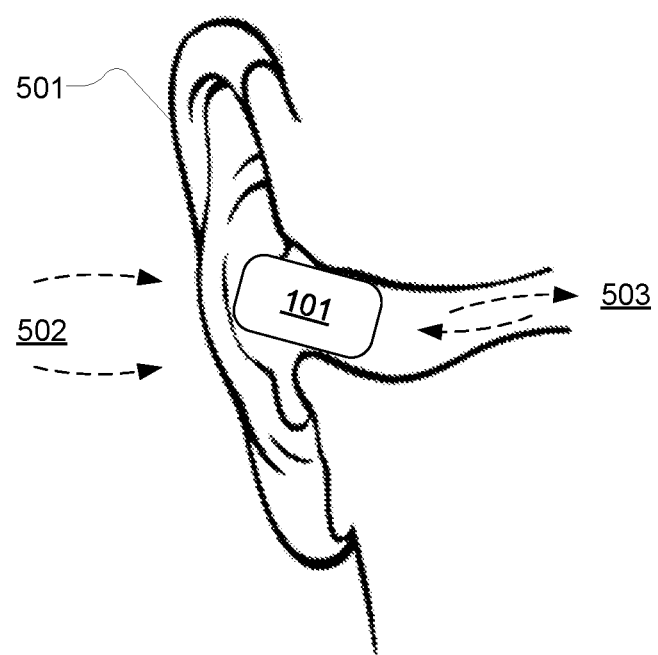
FIG. 5 shows an illustration of an ear with an electronic hearing device for capturing first acoustic signals from surroundings and second acoustic signals including otoacoustic emissions in response to a stimulation signal.

FIG. 5 shows an illustration of an ear 601 with an electronic hearing device 101 for capturing first acoustic signals 502 from surroundings and capturing second acoustic signals 503 including otoacoustic emissions in response to a stimulation signal.

In some examples, audiometric data may be provided by an external source; for example, the results of an audiogram testing process may be provided by an audiologist. The audiometric data can be input via a wireless connection into the electronic hearing device.

There is also provided an item as set out below:
1. a method performed by a hearing system at least including an electronic hearing device with an earpiece configured to be worn in an ear and including: an acoustic output transducer, a first acoustic input transducer, a second acoustic input transducer, a first wireless communications unit; and a processor coupled to the acoustic transducers; the method comprising;
   at a first time, performing a first monitoring procedure (240) including:
      emitting an otoacoustic stimulation signal via the acoustic output transducer (105) and capturing a second acoustic signal including otoacoustic emissions, if any, by means of the second acoustic input transducer (110);
   at least at a second time, performing the first monitoring procedure (310) including:
      emitting an otoacoustic stimulation signal via the acoustic output transducer and capturing a third acoustic signal including otoacoustic emissions, by means of the second acoustic input transducer;
      determining (303) a deviation value based on the second acoustic signal and the third acoustic signal; and determining whether the deviation value satisfies a first criterion;
   in accordance with a determination that the deviation value satisfies (y) the first criterion, communicating a first notification signal (305) indicative of the deviation from the hearing device.

Embodiments of the method defined in item 1 above, are set out in the present disclosure and in particular in dependent claims 2-12 and in claims 13-14.

Although particular features have been shown and described, it will be understood that they are not intended to limit the claimed invention, and it will be made obvious to those skilled in the art that various changes and modifications may be made without departing from the scope of the claimed invention. The specification and drawings are, accordingly to be regarded in an illustrative rather than restrictive sense. The claimed invention is intended to cover all alternatives, modifications, and equivalents.

The invention claimed is:
1. A method performed by a hearing system having a hearing device, the hearing device comprising an acoustic output transducer, a first acoustic input transducer, a second acoustic input transducer, a first wireless communications unit, and a processing unit, the method comprising:
obtaining a first acoustic signal by the first acoustic input transducer, and generating a compensated output signal based on the first acoustic signal, wherein the compensated output signal is based on current hearing compensation data;
performing a fitting procedure by: obtaining first hearing compensation data, emitting an otoacoustic stimulation signal via the acoustic output transducer, and obtaining a second acoustic signal by the second acoustic input transducer; and
performing a monitoring procedure if the second acoustic signal or data based on the second acoustic signal satisfies a first criterion, wherein the monitoring procedure is performed by:
emitting another otoacoustic stimulation signal via the acoustic output transducer, and obtaining a third acoustic signal by the second acoustic input transducer;
determining whether the third acoustic signal or data based on the third acoustic signal satisfies the first criterion;
determining a deviation value based on the second acoustic signal and the third acoustic signal if the third acoustic signal or the data based on the third acoustic signal satisfies the first criterion; and
in accordance with the deviation value satisfying a second criterion, outputting a first notification signal, the second criterion being different from the first criterion.

2. The method according to claim 1, wherein the hearing system also includes an electronic device having a display, an input component, a second wireless communications unit, and a processor.

3. The method according to claim 1, wherein the monitoring procedure is performed automatically without requiring a user's input.

4. The method according to claim 1, further comprising storing data values associated with the monitoring procedure;
wherein the data values include or are stored with a date-time value representing a time of obtaining the third acoustic signal.

5. The method according to claim 1, further comprising performing another fitting procedure by emitting a further otoacoustic stimulation signal via the acoustic output transducer, and obtaining a fourth acoustic signal by the second acoustic input transducer.

6. The method according to claim 1, after the fitting procedure is performed, providing a first notification prompting a user to engage the monitoring procedure, or providing a second notification prompting the user to engage another monitoring procedure.

7. The method according to claim 1, wherein the fitting procedure further comprises enabling the monitoring procedure by determining that the second acoustic signal or the data based on the second acoustic signal satisfies the first criterion.

8. The method according to claim 1, wherein the monitoring procedure is performed after receiving, by the hearing device, an input signal from an electronic device.

9. The method according to claim 1, further comprising:
providing the current hearing compensation data for storage as a first selectable item; and
providing the first hearing compensation data or second hearing compensation data for storage as a second selectable item;
wherein each of the first selectable item and the second selectable item is selectable.

10. The method according to claim 1, further comprising updating the current hearing compensation data based on the third acoustic signal.

11. The method according to claim 1, further comprising performing another fitting procedure to obtain second hearing compensation data, and updating the current hearing compensation data based on the second hearing compensation data.

12. The method according to claim 1, wherein the third acoustic signal is associated with the other otoacoustic stimulation signal.

13. The method according to claim 1, wherein the first hearing compensation data is based on audiometric measurements.

14. The method according to claim 1, wherein the monitoring procedure is performed in response to an input signal.

15. The method according to claim 1, wherein the hearing system comprises only the hearing device, and the method is performed by the hearing device.

16. A non-transitory processor-readable storage medium comprising one or more programs, the one or more programs including instructions for performing the method of claim 1.

17. A hearing device comprising:
an earpiece;
an acoustic output transducer;
a first acoustic input transducer;
a second acoustic input transducer;
a wireless communications unit;
a processing unit; and
a memory storing one or more programs, the one or more programs including instructions which, when executed by the processing unit, cause the method of claim 1 to be performed.

18. A hearing device comprising:
an earpiece;
an acoustic output transducer;
a first acoustic input transducer;
a second acoustic input transducer;
a wireless communications unit; and
a processing unit;
wherein the first acoustic input transducer is configured to obtain a first acoustic signal, wherein the hearing device is configured to generate a compensated output signal based on the first acoustic signal, wherein the compensated output signal is based on current hearing compensation data;
wherein the hearing device is configured to perform a fitting procedure by: obtaining first hearing compensation data, emitting an otoacoustic stimulation signal via the acoustic output transducer, and obtaining a second acoustic signal by the second acoustic input transducer; and
wherein the hearing device is configured to perform a monitoring procedure if the second acoustic signal or data based on the second acoustic signal satisfies a first criterion, wherein the hearing device is configured to perform the monitoring procedure by:
emitting another otoacoustic stimulation signal via the acoustic output transducer, and obtaining a third acoustic signal by the second acoustic input transducer;

determining whether the third acoustic signal or data based on the third acoustic signal satisfies the first criterion;

determining a deviation value based on the second acoustic signal and the third acoustic signal if the third acoustic signal or the data based on the third acoustic signal satisfies the first criterion; and in accordance with the deviation value satisfying a second criterion, outputting a notification signal, the second criterion being different from the first criterion.

19. The method according to claim 1, wherein the first criterion comprises a first threshold, and the second criterion comprises a second threshold different from the first threshold.

20. The hearing device according to claim 18, wherein the first criterion comprises a threshold, and the second criterion comprises a second threshold different from the first threshold.

* * * * *